United States Patent
Murakoshi et al.

(10) Patent No.: US 6,476,390 B1
(45) Date of Patent: Nov. 5, 2002

(54) METHOD AND APPARATUS FOR INSPECTING INTEGRATED CIRCUIT PATTERN USING A PLURALITY OF CHARGED PARTICLE BEAMS

(75) Inventors: Hisaya Murakoshi, Tokyo; Yusuke Yajima, Kodaira; Hiroyuki Shinada, Chofu; Mari Nozoe, Hino; Atsuko Takafuji, Tokyo; Kaoru Umemura, Musashino; Masaki Hasegawa, Hiki-gun; Katsuhiro Kuroda, Hachioji, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/646,281

(22) PCT Filed: Mar. 27, 1998

(86) PCT No.: PCT/JP98/01402

§ 371 (c)(1),
(2), (4) Date: Sep. 15, 2000

(87) PCT Pub. No.: WO99/50651

PCT Pub. Date: Jul. 10, 1999

(51) Int. Cl.$^7$ .......................... G01N 23/00; G21K 7/00
(52) U.S. Cl. ...................... 250/310; 250/306; 250/309; 250/311
(58) Field of Search ................. 250/310, 311, 250/441.11, 442.11, 492.1–492.24, 397–400, 306, 396 ML

(56) References Cited

U.S. PATENT DOCUMENTS

| | | | |
|---|---|---|---|
| 4,038,543 A | * | 7/1977 | Krisch et al. ............... 250/307 |
| 4,066,905 A | * | 1/1978 | Dassler et al. ........... 250/396 R |
| 4,596,929 A | * | 6/1986 | Coates et al. ............... 250/310 |
| 5,717,204 A | * | 2/1998 | Meisberger et al. ........ 250/310 |
| 6,046,459 A | * | 4/2000 | Yasutaka et al. ......... 250/492.2 |
| 6,225,632 B1 | * | 5/2001 | Kinno et al. ........... 250/370.09 |
| 6,236,053 B1 | * | 5/2001 | Shariv ........................ 250/397 |

OTHER PUBLICATIONS

"Electron–beam Microcolumns for lithography and related applications" J. Vac. Sci. Technol. B14(6), Nov./Dec. 1996, pp. 3774–3781.

* cited by examiner

Primary Examiner—John R. Lee
Assistant Examiner—David A. Vanore
(74) Attorney, Agent, or Firm—Antonelli, Terry, Stout & Kraus, LLP

(57) ABSTRACT

In a pattern inspection device of the present invention having at least three electron-optical systems, detection signals approximately simultaneously obtained from identical circuit patterns are compared with each other. Further, areas around plural electron sources can be maintained at high degrees of vacuum by evacuating an electron gun chamber mounted with plural electron guns independently of a sample chamber. Further, electric fields and magnetic fields are confined in each electron-optical system by a shield electrode which makes it possible to evacuate an electron beam path to a high degree of vacuum, and at the same time, secondary electrons and reflected electrons are detected in the same electron-optical system by setting the samples to a negative voltage and accelerating secondary electrons and reflected electrons toward the electron source side in the direction of the electron beam axis. Thus, defect determination in pattern inspection is performable substantially simultaneously, and at the same time, the throughput of the inspections is improvable in proportion to the number of the electron-optical systems. Further, three or more electron sources are operable in a stable manner in high vacuum states, and signals from closely arranged electron-optical systems are detectable with high accuracy, and accurate inspections are performable.

16 Claims, 13 Drawing Sheets

METHOD AND APPARATUS FOR INSPECTING INTEGRATED CIRCUIT PATTERN USING A PLURALITY OF CHARGED PARTICLE BEAMS

TECHNICAL FIELD

The present invention relates to a pattern inspection device and a pattern inspection method for semiconductors and the like, and, more particularly, to a pattern inspection device and a pattern inspection method which are capable of high-speed inspection of semiconductors and the like.

BACKGROUND OF THE INVENTION

In a semiconductor manufacturing process, a number of pattern formation steps are repeated. In the respective steps, if manufacturing conditions are not optimized, abnormalities such as foreign substances and defects and the like occur in a circuit pattern of a semiconductor device formed on a substrate. Accordingly, in the manufacturing process, it is necessary to detect the occurrence of an abnormality at an early stage and feed it back to the process.

Generally, in the manufacturing process for an VLSI or the like, as a number of chips having the same circuit pattern are obtained from one sheet of semiconductor substrate, a pattern abnormality is detected by comparing identical circuit patterns of different chips. In an inspection device to inspect a circuit pattern of a semiconductor wafer by using an electron beam, as it takes an enormous amount of time to inspect the entire wafer with the electron beam, a method to compare identical circuit patterns of different chips, by a construction having two electron-optic systems is especially disclosed in Japanese Published Unexamined Patent Application No. Sho 59-6537.

As is well-known in the art, if a difference signal of detection signals, obtained from identical circuit patterns of different chips, exceeds a reference value, it is determined that a pattern abnormality exists. However, in this construction, although it can be determined that an abnormality exists in one of the chips, the chip having the abnormal pattern cannot be determined. In the abnormality determination, comparison with another pattern obtained from another chip is necessary. For this purpose, all the image data of the two chips is stored into an image memory, then the inspection moves to another chip, the electron beam is emitted on the corresponding same pattern, and a determination is made. Accordingly, a large capacity image memory is required, and further, there is a possibility that the stability of the system is impaired with the lapse of time during movement to the other chip.

Further, to improve the throughput of the inspection time, it is necessary to emit a fine electron probe beam of large current on a sample. For this purpose, the brightness of an electron beam source must be high, so that a field-emission type electron source is indispensable as the electron beam source. Note that to operate the field-emission type electron beam source in a stable manner, the degree of vacuum around the electron beam source must be suppressed to the order of $10^{-7}$ Pa. However, in the conventional construction, it is difficult to closely arrange plural electron-optic systems with maintaining a high vacuum degree in the electron beam guns. For example, in the above-described well-known art, an area around the electron beam source is evacuated from a sample chamber. Further, in a conventional technique described in "Journal of Vacuum Science and Technology B14(6)", page 3776, the entire electron-optical system is placed in one chamber, as shown in FIG. 12. Accordingly, in this construction, to evacuate the area around the electron beam source to a very high degree of vacuum, the sample chamber must be also evacuated to a very high degree of vacuum. However, since a wafer coated with chemical material, such as a resist, emits a large amount of gas, and the structure of a stage to control movement of the wafer is complicated, it is practically impossible to evacuate the sample chamber to a very high degree of vacuum. Generally, the degree of vacuum is merely improved to about $10^{-5}$ Pa. Even if a very high degree of vacuum in the sample chamber can be realized, as the degree of vacuum in the sample chamber is lowered upon exchange of a sample, the period to evacuate the sample chamber after the sample exchange to the very high degree of vacuum is e.g. equal to or longer than one hour. Thus, it is impossible to inspect a large number of wafers within a short period, Further, in a construction as shown in FIG. 13 where an electron beam gun chamber 101 and a sample chamber 103 are respectively evacuated by independent vacuum pumps, a large number of vacuum pumps must be provided, with the result that a large number of spaces for placement of vacuum pumps must be provided. For example, in FIG. 13, to provide a vacuum pump for the central electron-optical system, a close arrangement is impossible.

Further, in general detection means, if the electron-optical systems are closely arranged, it is difficult to hold secondary electrons and reflected electrons 302 obtained by emitting an electron beam on a sample within the same electron-optical system. That is, as means for detecting the secondary electrons and reflected electrons 302 in plural electron-optical systems, a method for detection by providing detectors 13 on the rear surfaces of final stage lenses, as shown in FIG. 15, is disclosed in the "Journal of Vacuum Science and Technology B14(6)" page 3775. In this construction, it is difficult to hold the secondary electrons and reflected electrons 302 within the same electron-optical system, and so the secondary electrons and reflected electrons 302 are easily attracted by the detector 13 in the adjacent electron-optical system; as a result, precise pattern inspection cannot be made. Further, Japanese Published Unexamined Patent Application No. Hei 2-142045 discloses a method for detecting secondary electrons, accelerated by application of a negative voltage to a sample, that have passed through an objective lens. However, there is no specific construction to improve the efficiency of secondary electron detection.

SUMMARY OF THE INVENTION

The present invention has the following construction as means for solving the above problems. That is, at least three electron-optical systems are provided, and detection signals from identical circuit patterns of different chips are compared with each other. If three or more images are obtained at the same time, the position of a pattern defect can be simultaneously determined. Further, in a case where a stage is continuously moved, the same pattern repeatedly exists within the chip, and images continuously obtained by the respective electron-optical systems are sequentially compared, the throughput of the inspection period is improved in proportion to the number of electron-optical systems.

Further, in accordance with the present invention, as shown in FIG. 14, to maintain a high degree of vacuum in an area around the electron source 1, three or more electron-optical systems are provided in one mirror body representing a same column or chamber, and a common vacuum pump evacuates an area around the electron source 1 or an area around an intermediate chamber 102 provided between the electron source 1 and the sample chamber 103, so that the electron-optic systems can be closely arranged. That is, since the areas around the plural electron sources 1 are connected to the area around the sample chamber via fine openings through which electron beams pass, and the areas around the electron sources are evacuated independently of the area around the sample chamber 103, a high degree of vacuum in the areas around the electron sources 1 can be maintained.

Further, to independently detect secondary electrons and reflected electrons, produced in the plural electron-optical systems, in the respective electron-optical systems, the secondary electrons and reflected electrons 302, generated from the sample are accelerated toward the electron source side in the direction of the electron beam axis 9 so that they can be detected by a detector provided toward the electron source side from an objective lens, without colliding against a counter electrode 19, as shown in FIG. 16. The vertical-directional speed of the secondary electrons and reflected electrons-302 on the electron beam axis 9 is constant from a point where they are emitted from the sample. As the speed is accelerated in the direction of electron beam axis 9, the trajectories of the secondary electrons and reflected electrons 302 are directed toward the electron beam axis 9. Then, a voltage U is applied between a sample 10 and the counter electrode 19 opposite to the sample 10, and if the sample 10 is not tilted, but is placed approximately in parallel with the counter electrode 19, an approximately uniform electric field parallel to the sample is distributed between the sample 10 and the counter electrode 19. Then, assuming that it is a parallel electric field, a distance R from a point where an electron is emitted in a direction approximately parallel to the surface of the sample, to a point where the electron reaches the counter electrode is expressed by the following expression, where L is the distance between the sample and the electrode and eV is the energy of electron emitted from the sample.

$$R = 2\sqrt{\frac{eV}{eU}} L \quad (1)$$

Actually, if the counter electrode 19 has an opening, the electric field is not a parallel electric field around the opening, however, the distance R can be approximated by the expression (1). Considering a scan width S by a primary electron beam on the sample, an area where the electrons emitted from the sample spread at the counter electrode is 2R+S. Accordingly, in a case where the value R is obtained by substituting the maximum energy of the reflected electron i.e. the energy of the primary electron beam into the energy of an emitted electron in the expression (1) as Rmax, and a diameter D1 of the counter electrode is $$D1 > 2 Rmax+S \quad (2),$$

the reflected electrons and secondary electrons are not dissipated outward from the counter electrode, and can be collected within the same optical system. Further, in a case where the value R is obtained by substituting 50 eV into the energy eV in the expression (1) as Rse, and a diameter D2 of the opening of the counter electrode 19 is $$D2 > 2 Rse+S \quad (3),$$

all the secondary electrons or reflected electrons having an energy equal to or less than 50 eV pass through the opening of the counter electrode toward the electron source side. Note that if the scan width S is sufficiently small, the expressions (2) and (3) can be omitted. If the sizes of the counter electrode and the openings of the counter electrodes are set according to the above-described conditions, the secondary electrons or reflected electrons generated from the sample can be efficiently detected without being dissipated to the adjacent optical system. The secondary electrons and reflected electrons 302 which have passed through the opening of the counter electrode are acted upon by an objective lens 4. The detectors 13 are provided above the objective lens 4, and can detect almost all of the secondary electrons and reflected electrons 302 on trajectories that are changed by the action of the objective lens. As the secondary electrons and reflected electrons 302 are detected in this manner, even in a condition where plural electron-optical systems are closely arranged, the secondary electrons and reflected electrons 302 can be efficiency detected without being dissipated to the adjacent optical system. Further, in a construction where a primary electron beam 301 is almost not deflected, but the secondary electrons and reflected electrons 302 are deflected, e.g., in a construction where a deflector having an intersecting magnetic field and electric field is provided such that the secondary electrons and reflected electrons 302, accelerated in the electron-beam axis direction, pass through the deflector, the secondary electrons and reflected electrons 302 can be more efficiently detected. Further, an opening aperture to limit an opening angle of the primary electron beam is provided toward the electron source side from the detector such that the secondary electrons or reflected electrons do not collide against the opening aperture.

Further, in accordance with the present invention, to avoid any influence by the electromagnetic field produced in each optical system on peripheral electron-optical systems, as shown in FIG. 14, a shielded electrode 17, having a structure to confine the electric field or magnetic field produced in each electron-optical system within the optical system and means to evacuate an electron beam passage to a very high degree of vacuum, is provided in an outer periphery of the electron-optical system, such that an electric field and magnetic field leaking from the electronic lens and the detector can be closed within the same optical system.

In the above construction, as three or more electron-optical systems are closely arranged within the same mirror body or column and a pattern defect is determined in real time, the inspection accuracy can be improved and the inspection speed can be increased in proportion to the number of electron-optical systems. Further, as the degree of vacuum in the areas around the three or more electron sources are maintained at a high degree of vacuum, even in the sample chamber which is in a low vacuum state, e.g., upon sample exchange, the electron sources can be operated in a stable manner. Further, since an electron beam is not deflected from another electron-optical system, a signal detected from a pattern can be independently detected with high accuracy within each electron-optical system. Accordingly, pattern inspection can be performed at a high speed and with high accuracy.

BEST MODE FOR CARRYING OUT THE INVENTION

The present invention will be described with reference to various embodiments. A first embodiment of the present invention is applied to a semiconductor pattern circuit inspection, and will be described with reference to FIGS. 1 and 2.

Figure 2:
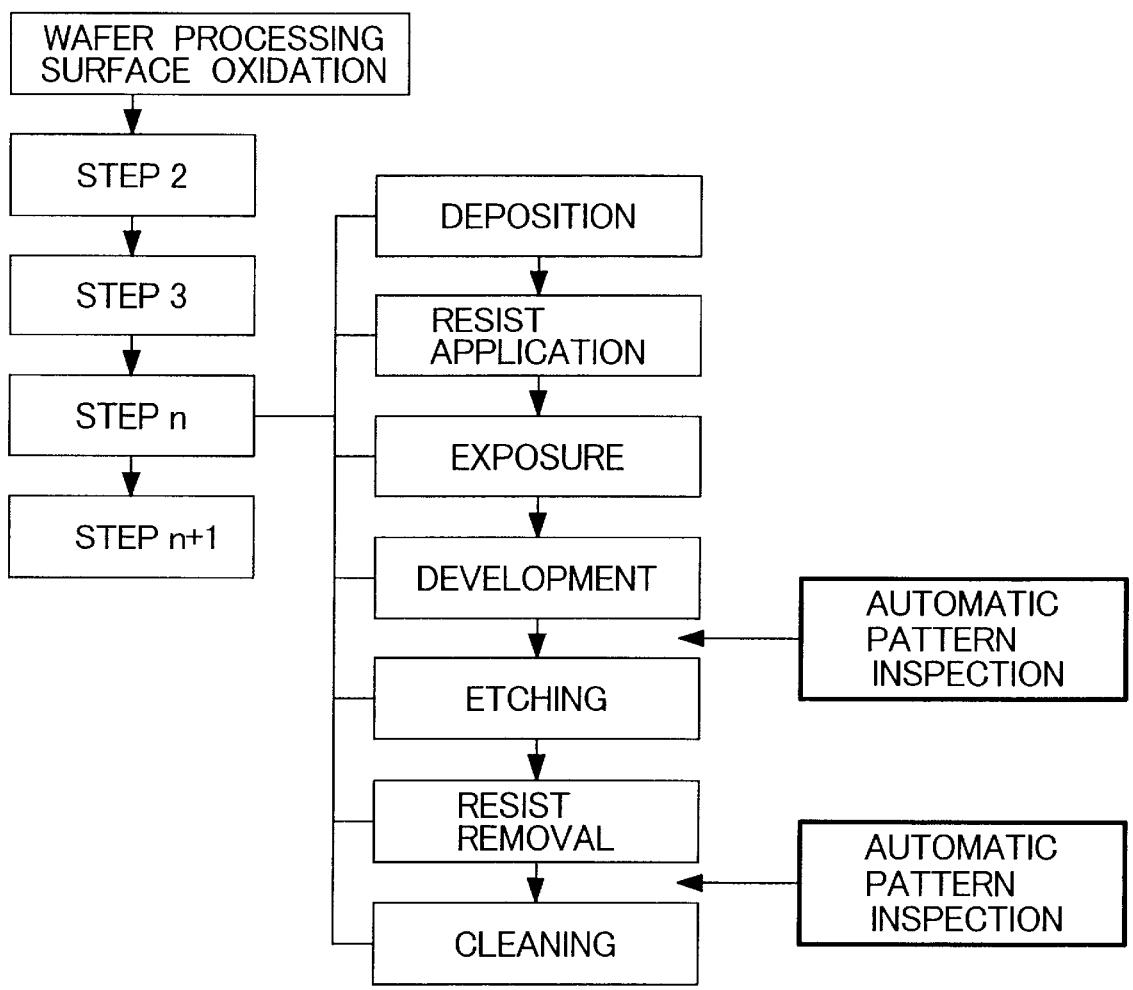
FIG. 2 is a flow diagram showing a procedure employed by the first embodiment of the present invention.

As shown in FIG. 2, in a semiconductor device manufacturing process, a large number of pattern formation steps are repeated. A pattern formation step briefly includes steps of film formation, photo-resist coating, photosensitizing, development, etching, resist removal and cleaning. If manufacturing conditions are not optimized in the respective steps, the circuit pattern of semiconductor device formed on a substrate will not be normally formed. For example, if an abnormality occurs at the film formation step, particles occur and are attached to the surface of wafer, and an isolation defect and the like will occur. Further, if conditions such as during the focus and exposure period are not optimized upon resist photosensitizing, the amount and intensity of emitted light will be partially great and high, and partially small and low, so that a short circuit, a break and pattern thinning may occur. If there is a defect in a mask and/or a reticle upon exposure, a similar abnormality easily occurs in the pattern formation. Further, if the etching amount is not optimized or a thin film and/or particles are produced in the middle of etching, a short circuit, projection(s), isolation defect(s), as well as poor opening formation and the like may occur. Upon cleaning, an abnormal oxidation easily occurs at a pattern corner and the like by a water drain condition or the like in drying. Accordingly, in the wafer manufacturing process, the process conditions must be optimized so as to avoid such failures, and the occurrence of an abnormality must be detected at an early stage and fed back to the process. In the present embodiment, an example of inspection after the resist photosensitizing and the development in the n-th pattern formation process will be described.

Figure 1:
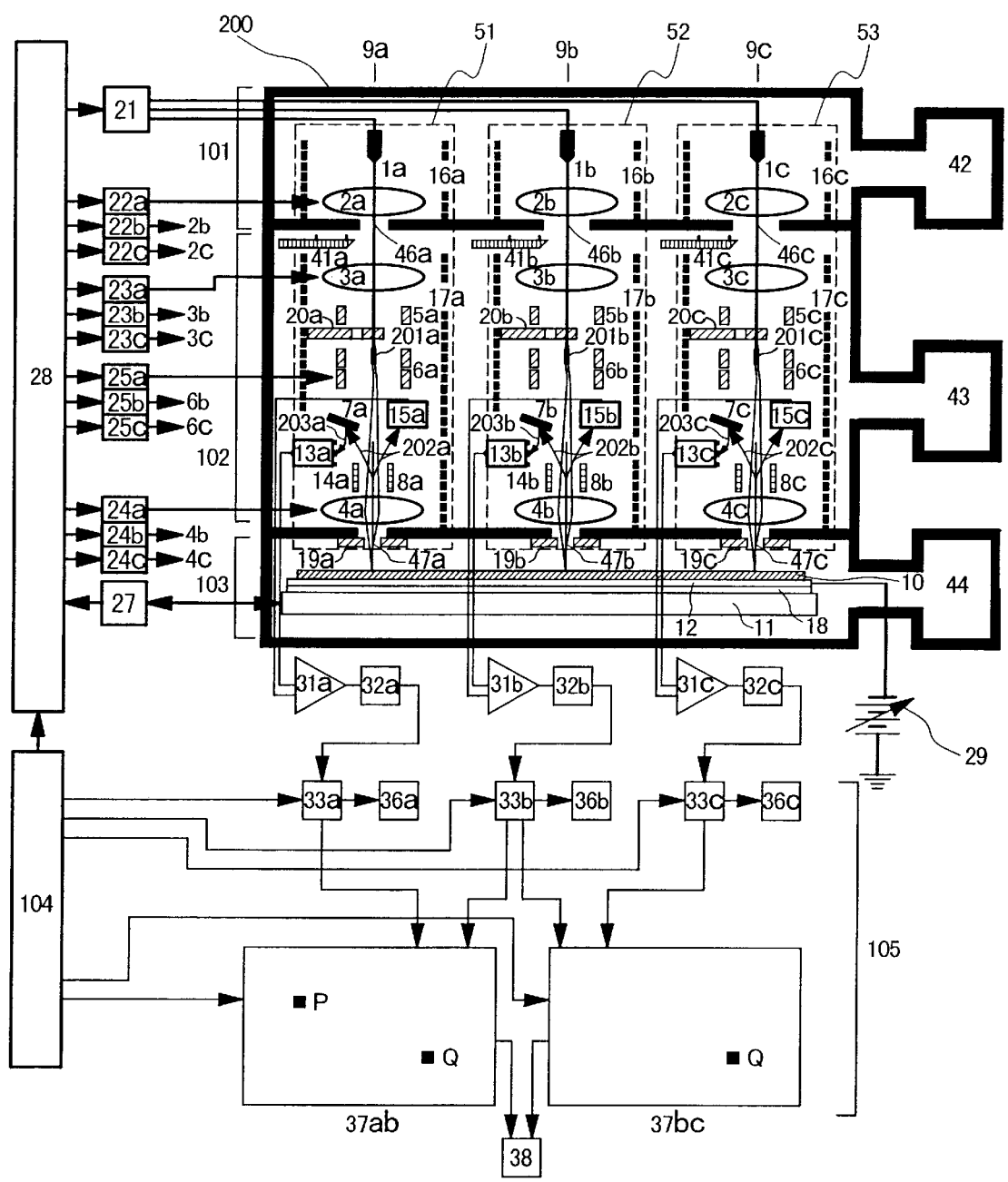
FIG. 1 is a diagram showing a first embodiment of the present invention.

An embodiment for effecting inspection will be described in detail. FIG. 1 shows the structure of the embodiment.

An electron-optical arrangement, including three systems, a first electron-optical system 51, a second electron-optical system 52 and a third electron-optical system 53, has a close arrangement where these electron-optical systems are arranged within one mirror body 200 representing a same column or chamber. Since the respective electron-optical systems have the same structure, in the following description, indication of the respective elements will be simplified. For example, the respective optical systems have electron sources 1a, 1b and 1c, however, the electron sources will be described as an electron source 1. Similarly, the respective optical systems have other components shown in the drawings as a, b and c with an appropriate reference number, but only referred to herein by its reference number. The electron-optical system has an electron source 1, an electron gun lens 2, a condenser lens 3, an objective lens 4, a blanking deflector 5, a scan deflector 6, a reflection plate 7 and an E×B deflector 8. A sample chamber 102 has an X-Y stage 11, a pallet 12 to hold a sample, a spacer 18 and a position-monitoring length-measuring instrument 27. A detector 13 is positioned above the objective lens 4, and an output signal from the detector 13 is amplified by a preamplifier 31, and converted into digital data by an AD converter 32. An image processor 105 has an image memory 33, a calculator 37 and a defect determination unit 38. A read electron beam image is displayed on a monitor 36. Operation commands and operation conditions for the respective elements of the inspection device are inputted/outputted into/from a controller 104. Conditions such as an acceleration voltage upon generation of an electron-beam, an electron-beam deflection width, a deflection speed, a moving speed of the sample stage, and signal-reading timing for the detector are inputted to the controller 104 in advance. Further, the controller 104 generates a correction signal from a signal received from the position-monitoring length-measuring instrument 27, and sends the correction signal from a correction controller 28 to a lens power source and a scan signal generator 25 so as to emit an electron beam onto an always correct position.

A primary electron beam emitted from the field-emission type electron source 1 is accelerated to a desired acceleration voltage by the electron gun lens 2, then is focused on the sample by the condenser lens 3 and the objective lens 4. Reflected electrons reflected from the sample or secondary electrons secondarily generated in the sample are detected by the detector 13, then amplified by the preamplifier 31 and AD-converted by the AD converter 32, then stored into the image memory 33, and, at the same time, an image is displayed on the monitor 36. The primary electron beam is deflect-scanned by the controller 104 by effecting control of the primary electron beam based on a scan signal sent from the scan signal generator 25.

A field-emission type electron source is employed as the electron source 1. Especially in pattern circuit inspection, a diffused replenish type thermal field-emission electron source is desirable. By using this type of electron source, since comparison inspection images with reduced brightness variation can be obtained, and the electron beam stream can be enlarged, high-speed inspection can be performed. The electron lenses of the respective electron-optic systems are controlled as follows.

The primary electron beam is pulled out of the electron source 1 by application of voltage to the electron gun lens 2. The primary electron beam is accelerated by application of a negative high voltage from an electron-source application high-voltage source 21 to the electron source. By this acceleration, the primary electron beam with energy corresponding to the potential, e.g., 10 kV, proceeds toward the sample stage 11. A negative voltage from a retarding high voltage source 29 can be applied to the pallet 12, which is electrically insulated from the X-Y stage 11 via the spacer 18. The sample 10 held on the pallet 12 is set to the same potential as that of the pallet 12. By controlling the voltage of the retarding high voltage source 29, the electron-beam emission energy to the sample 10 can be easily controlled to an optimum value. The acceleration voltage supplied to the electron source 1 from the electron-source application high-voltage source 21 and the voltage applied to the pallet 12 are the same in the respective electron-optical systems so as to attain the same energy of the primary electron beams incident on the sample in all the electron-optical systems. On the other hand, the voltage applied to a pull-out electrode in the electron gun lens 2 can be controlled independently in the respective electron-optical systems, and as the voltages are supplied from the respective electron gun power sources 22a, 22b and 22c, the currents from the electron sources can be independently controlled. The primary electron beams, which have passed through the electron gun lenses 2, are focus-emitted onto the sample 10, representing in inspected substrates (wafer, chip or the like) placed on the X-Y stage 11, with arbitrary magnifications, by independently controlling the condenser lens power sources 23a, 23b and 23c and objective lens power sources 24a, 24b and 24c. The X-Y stage 11 continuously moves during the inspection.

To obtain an image of the sample 10, the primary electron beam, which is shaped to be thin, is emitted on the sample 10, to cause the generation of secondary electrons, and the electrons are detected in synchronization with the scanning of the primary electron beam and the movement of the stage. Thus, an image of the sample surface is obtained. In automatic pattern inspection as described in accordance with the present invention, a fast inspection speed is necessary. Accordingly, low-speed emission of a pA order beam stream as in a general SEM is not performed. An image is formed by once or several times of scanning of the electron beam of a large current of about 100 times e.g. 100 nA in comparison with that of the general SEM. For example, in one image, 1000×1000 pixels are obtained for 10 msec.

Pattern comparison between chips can be performed in realtime from images obtained by approximately simultaneously irradiating identical pattern portions of different chips using the three electron-optical systems. That is, in the image processing system 105, a pattern image from the first electron-optical system 51, stored in the image memory 33a, a pattern image from the second electron-optical system 52, stored in the image memory 33b, and a pattern image from the third electron-optical system 53, stored in the image memory 33c, are compared with each other, and defect determination on the circuit substrate is performed in realtime. First, in the image processing system 105, a calculator 37ab performs a calculation for the pattern images stored in the image memories 33a and 33b. For example, the calculator 37ab has a function to obtain the difference between both images, and stores an address of an image with a difference between both images over a certain threshold value. For example, as shown in FIG. 1, it is determined that there are defects at addresses P and Q. However, the image having the defects cannot be determined by comparison between two images. Thus, at approximately the same time, the calculator 37bc performs a calculation for the pattern images stored in the image memories 33b and 33c. For example, in a case where a defect is displayed only in the position Q as shown in FIG. 1, since the defect always appears in the position Q in a comparison including the image b, the defect determination unit 38 determines that the defect at the position Q is included in the image in the image memory 33b, and determines that the defect at the position P is included in the image in the image memory 33a. In this manner, pattern defect determination can be performed in real time by approximately simultaneously obtaining images of identical patterns from different chips by using the three electron-optical systems. In this case, comparison among three image has been described, however, even in case of simultaneous comparison among four or more images, an image having a defect can be determined by an approximately similar algorithm.

Figure 3:
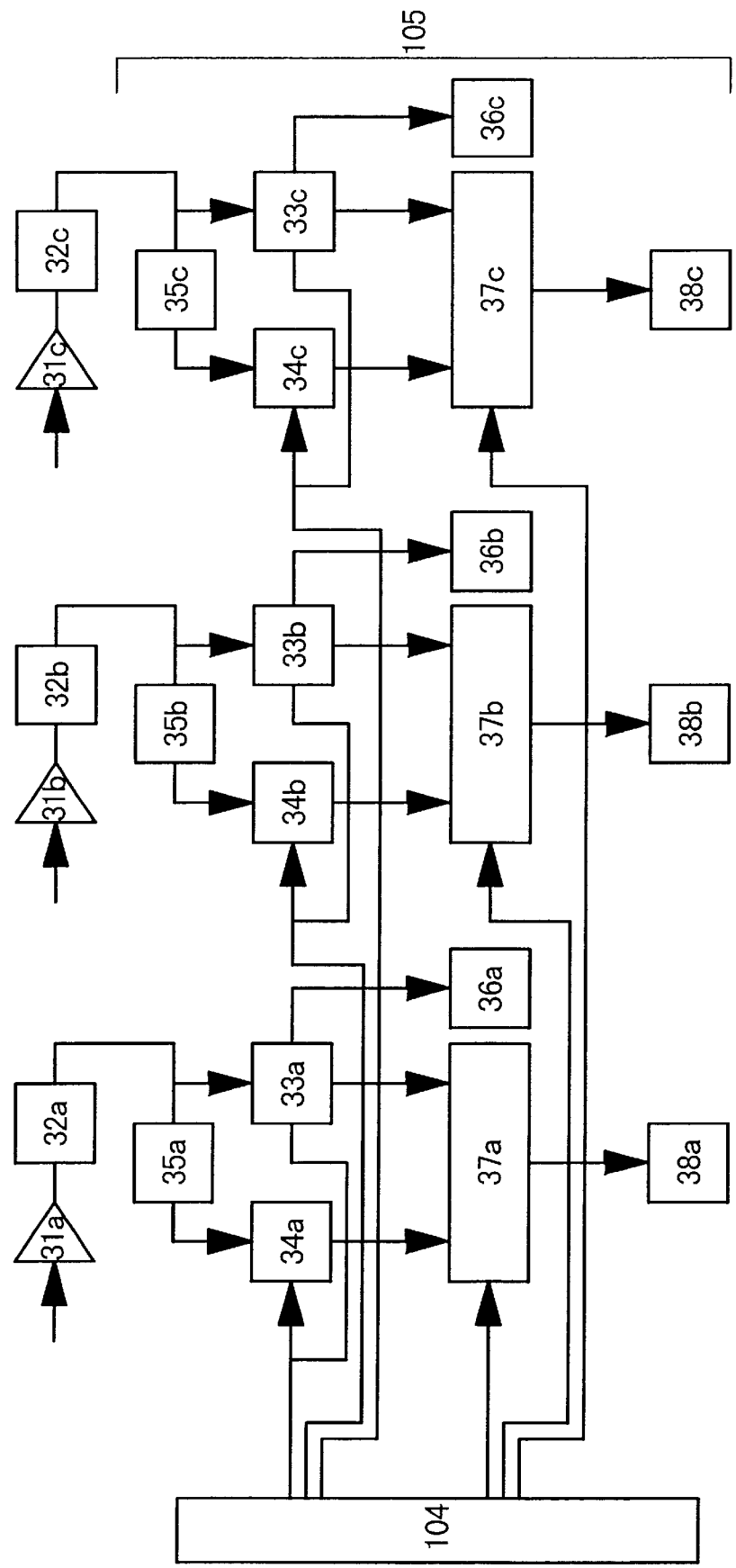
FIG. 3 is a block diagram showing another construction of an image processing system according to the first embodiment of the present invention.

Next, FIG. 3 shows the construction of the image processing system 105 which operates to sequentially compare images obtained in the respective optical systems and detect a defect. If the same pattern is repeatedly drawn in the chip as in the case of a semiconductor memory pattern, a defect can be detected by sequentially comparing images obtained in the respective optical systems. In the image processing system 105, comparison and evaluation are performed between an image stored in the image memory 33 in each optical system and an image delayed for one image by a delay circuit 35 and stored in an image memory 34. The calculator 37 has a function to calculate a difference between e.g. both images, and stores an address P of an image with a difference over a certain threshold value into the defect determination unit 38. If the address P corresponds with an address stored as a defect in the previous comparison, the defect determination unit 38 determines that the defect at the address P is a defect included in the image stored in the image memory 33. In this order, the defect search on circuit board is performed. In case of defect detection by this sequential image comparison, the pattern defect inspection speed increases in proportion to the number of electron-optical systems, and the defect inspection period can be reduced by providing a large number of electron-optical systems.

Next, means for independent operation of a detection system in each electron-optical system will be described. In accordance with the present invention, the secondary electrons and reflected electrons 202 generated from the sample are accelerated toward the electron source 1 side in the direction of the electron beam axis 9, to prevent the secondary electrons and reflected electrons 202 from spreading in a direction transverse to the electron beam axis 9 and enter the adjacent optical system. The sample 10 is set to a negative potential, and the primary electron beam 201 is radically decelerated immediately in front of the sample 10. The reflected electrons reflected from the sample 10 or the secondary electrons secondarily produced in the sample 10 are accelerated toward the electron beam axis 9. Assuming that the primary electron beam 201 is decelerated from 10 kV to 500 eV on the sample, the reflected electrons or secondary electrons are accelerated by a voltage of 0.5 kV applied between the sample 10 and the counter-electrode 19. Assuming that the distance between the sample 10 and the counter electrode 19 is 5 mm and the scan width of the primary electron beam is 0.1 mm, if the diameter of the counter electrode 19 is set to about 5 mm or longer in accordance with the expression (2), all of the secondary electrons or reflected electrons generated from the sample are directed along trajectories inside of the counter electrode, thus the entrance of the electrons into the adjacent optical system can be prevented. Further, by setting the diameter of an opening 47 to about 1.6 mm or longer in accordance with the expression (3), the reflected electrons or secondary electrons of 50 eV or less can be passed inside the opening 47. The reflected electrons or secondary electrons, which have passed through the objective lens 4, are deflected toward a detector 15 by the E×B deflector 8, and are directly detected by the detector 15. Otherwise, the secondary electrons or reflected electrons 202 are accelerated toward the electron beam axis 9, then deflected toward the reflection plate 7 by the E×B deflector 8, and collide against the reflection plate 7 to generate the second secondary electrons 203. The second secondary electrons 203 are detected by the detector 13, which is set to a positive potential higher than that of the reflection plate 17. Further, the position of the aperture 20 to limit the emission angle of the primary electron beam on the sample is arranged toward the electron source side from the detector 13 or the detector 15, so that the secondary electrons or reflected electrons can be efficiently detected without colliding against the aperture 20.

Figure 9:
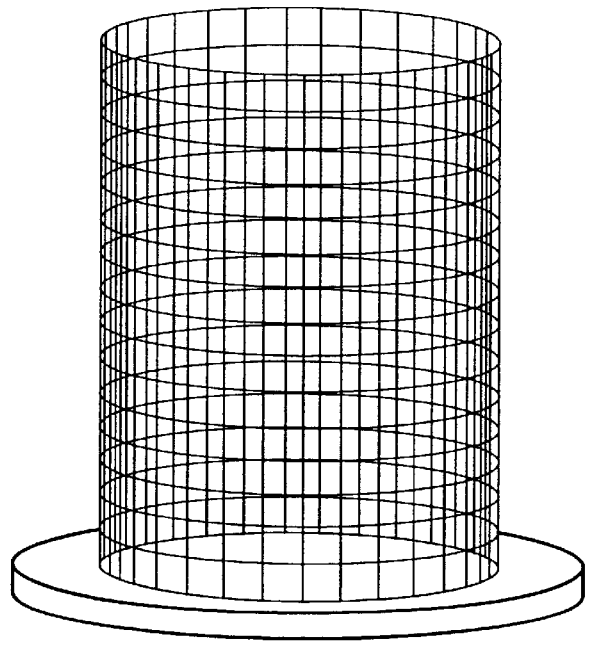
FIGS. 9, 10, 11(a) and 11(b) are diagrams showing the structure of a shielded electrode.
Figure 10:
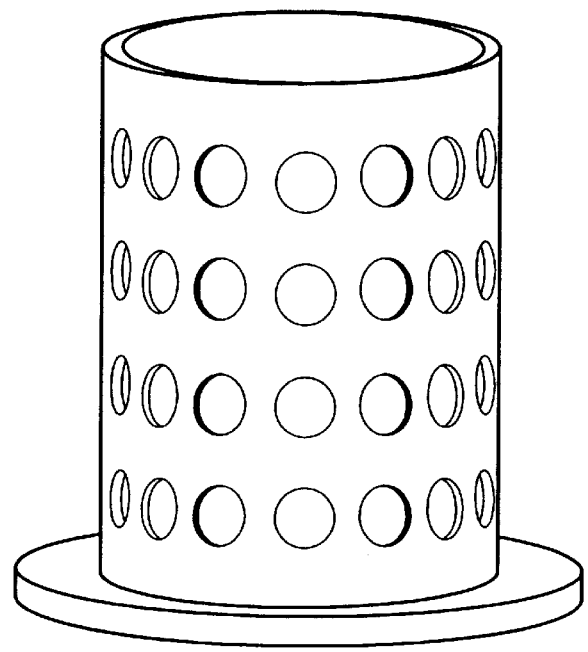
Figure 11A:
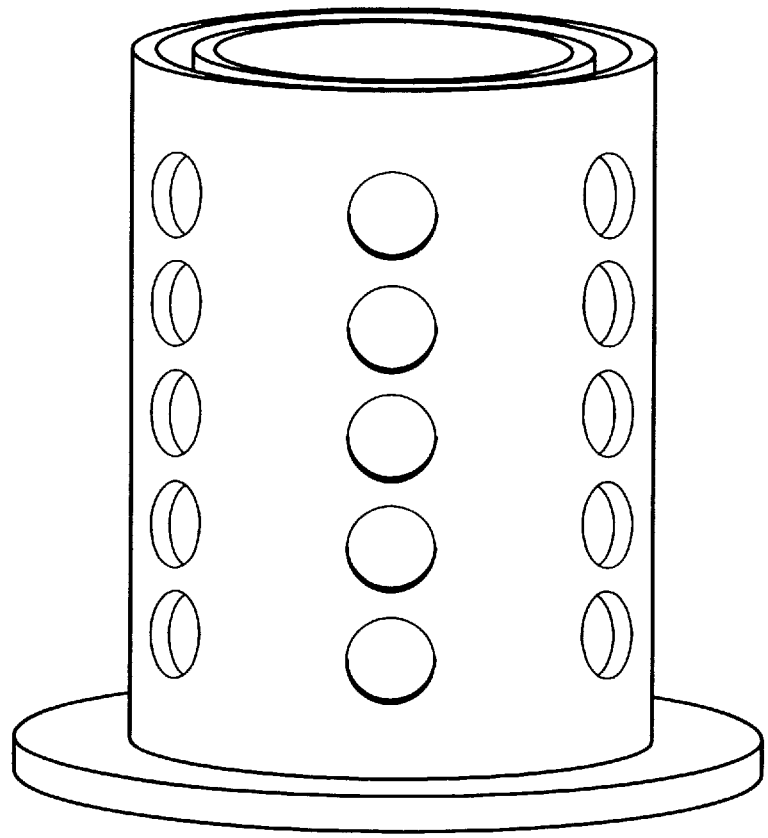
Figure 11B:
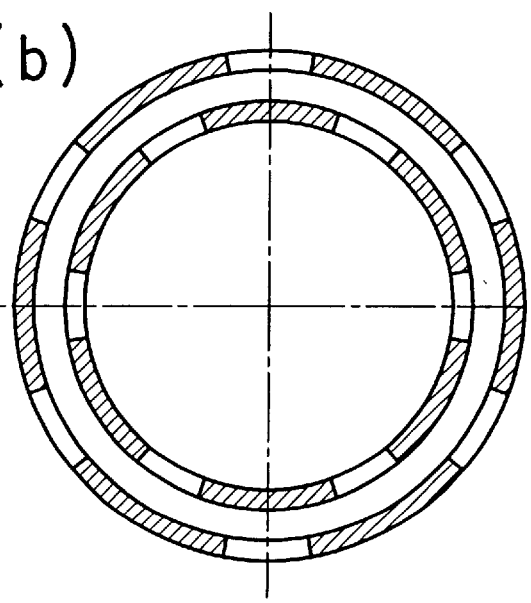
Figure 12:
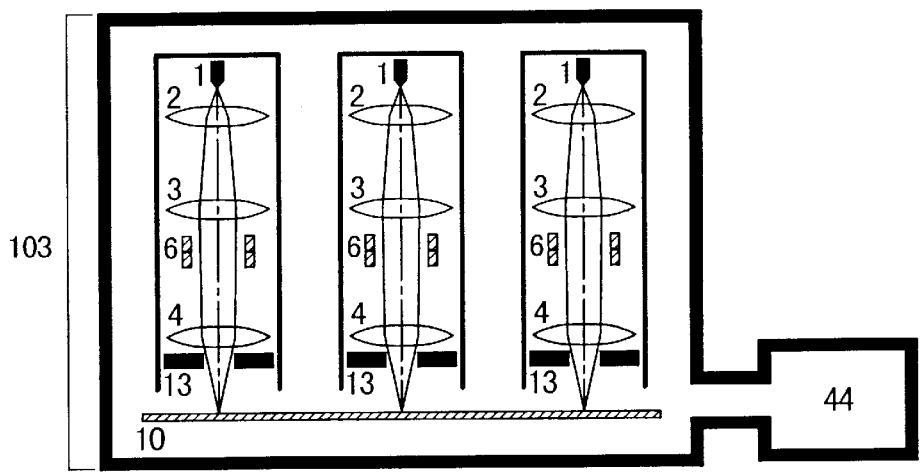
FIG. 12 is a diagram showing plural electron-optical system disposed in one chamber.
Figure 13:
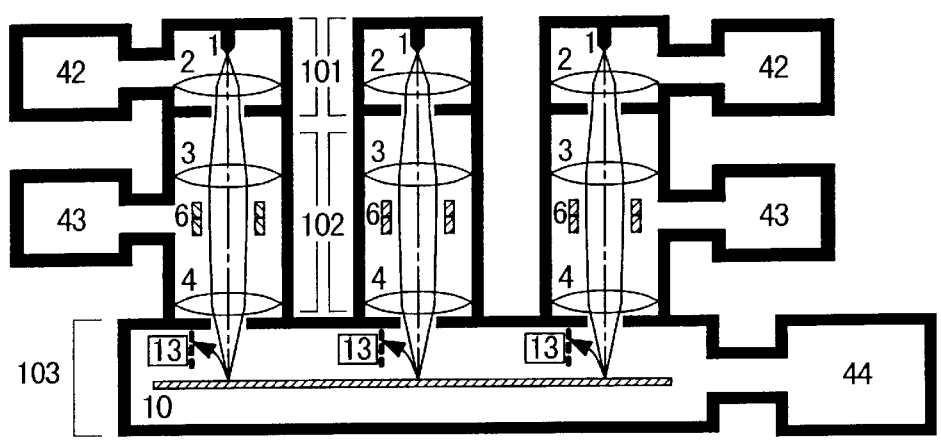
FIG. 13 is a diagram showing electron-optical systems in which the electron beam chambers, the optical chambers and the sample chamber are evacuated by separate vacuum pumps.
Figure 14:
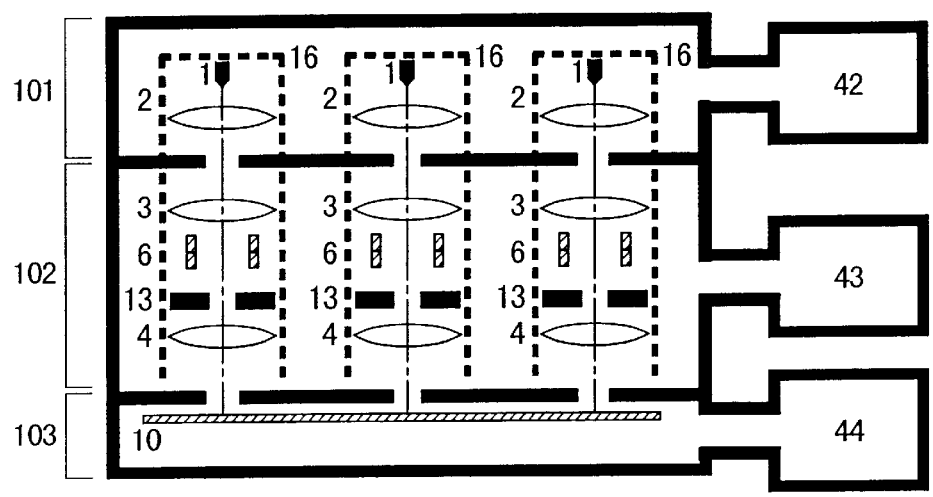
FIG. 14 is a diagram in which plural electron-optical systems are disposed in one chamber which is divided into sections that are individually evacuated by separate vacuum pumps.
Figure 15:
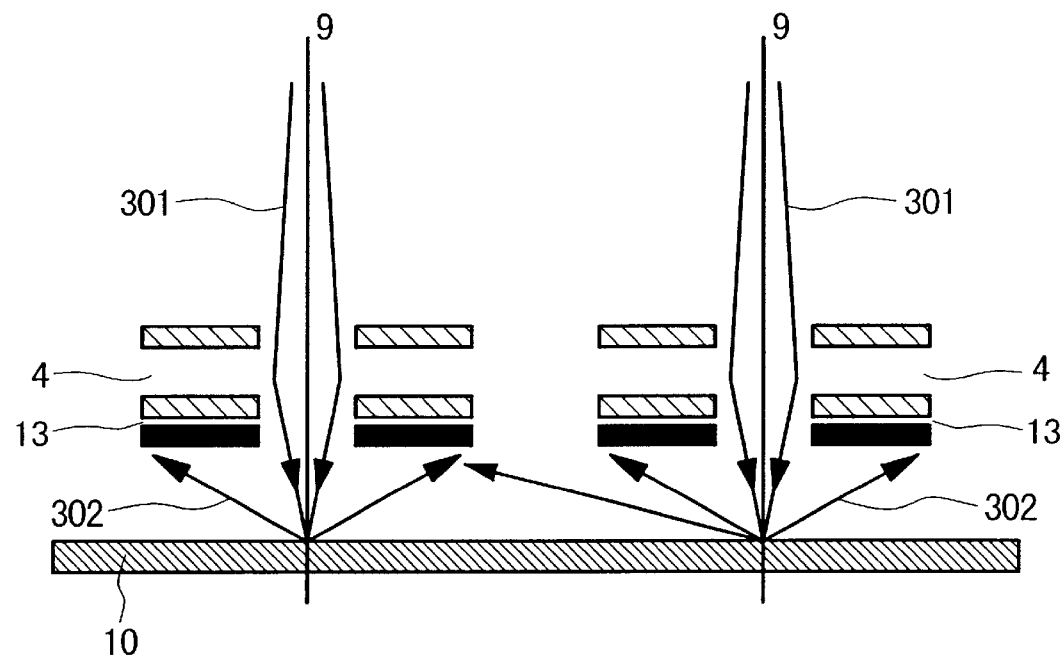
FIG. 15 is a diagram of electron-optical systems using detectors on the rear surfaces of final stage lenses.
Figure 16:
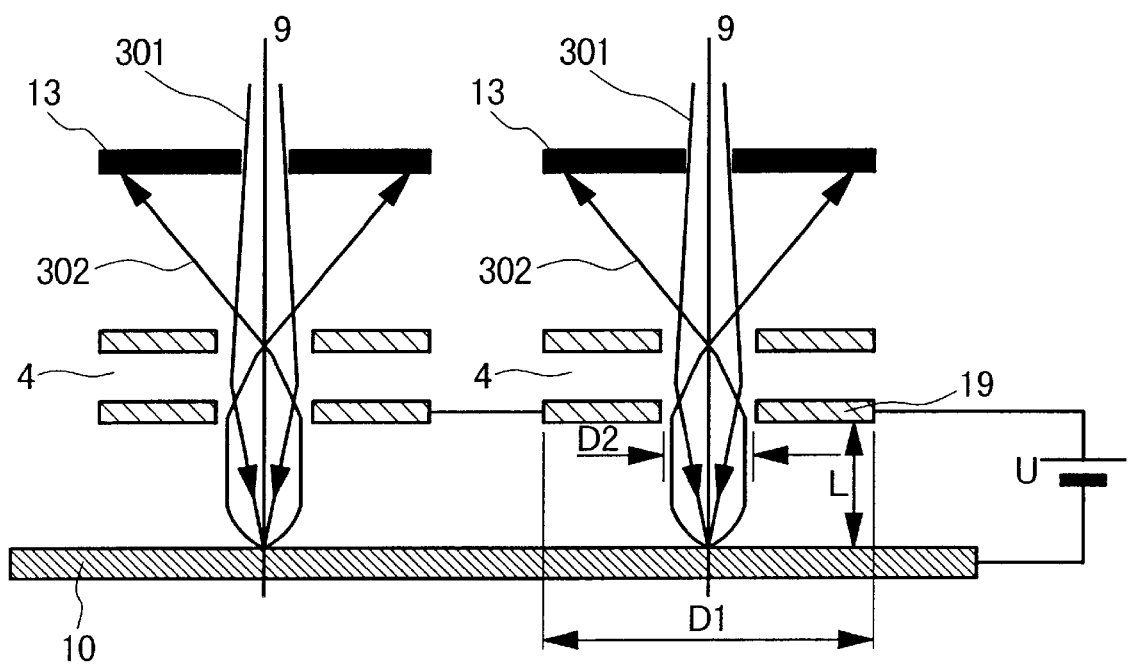
FIG. 16 is a diagram of electron-optical systems in which a detector is provided toward the electron source side from an objective lens.

Further, means for independently operating the respective optical systems by confining electric fields and magnetic fields produced in each electron-optical system within the same optical system will be described. Shield electrodes of conductor magnetic material are grounded on the outer periphery of each electron-optical system, thus the electromagnetic field in the electron-optical system is confined within approximately the same optical system. That is, a shield electrode 16 provided to shield electromagnetic fields of the electron source 1 and the electron gun lens 2 is provided in an electron gun chamber 101, and a shield electrode 17 to shield electromagnetic fields of the condenser lens 3, the objective lens 4 and the scan deflector 6 is provided in an intermediate chamber 102. Especially, if electromagnetic fields of the E×B deflector 8 and the detector 13 are leaked lo the adjacent optical system, electrons produced in the adjacent optical system are also drawn. Accordingly, in this construction, the effect of confining the electromagnetic fields around the E×B deflector 8 and the detector 13 is increased. These shield electrodes also have effects to shield external floating electromagnetic fields. The shield electrodes may have any shape as long as it has an electromagnetic field confining effect and it is possible to evacuate the electron beam passage to a high degree of vacuum. For example, the electrodes may have a mesh cylindrical shape as shown in FIG. 9, or may have a cylindrical shape with openings for evacuation as shown in FIG. 10. Further, if the electrodes have a shape as shown in FIGS. 11(a) and 11(b), with a multiple structure such as double or more structure with openings in a staggered arrangement, the shielding effect can be further improved almost without degradation of conductance of evacuation.

Next, means for operating the electron source always in a high vacuum state will be described. In the present embodiment, three or more electron-optical systems are provided within one mirror body 200 representing a same column. The spaces of the electron gun chamber 101 including the electron source 1 and the electron source lens 2, the intermediate chamber 102 and the sample chamber 103 are respectively evacuated by independent vacuum pumps 42, 43 and 44. It is desirable that the respective spaces are independently evacuated, however, the electron beam passage through which the primary electron beam 201 emitted on the sample 10 passes is necessary. That is, the electron gun chamber 101 and the intermediate chamber 102 are connected with each other via an opening 46, and the intermediate chamber 102 and the sample chamber 103 are connected with each other via the opening 47. Accordingly, especially while the primary electron beam 201 is emitted from the electron source 1, to evacuate the respective spaces as independently as possible, the electron beam passage including the opening 46 and the opening 47 have the greatest conductance between the electron gun chamber 101 and the intermediate chamber 102, and between the intermediate chamber 102 and the sample chamber 103 or between the electron gun chamber 101 and the sample chamber 103. In this construction, the degree of vacuum in the electron gun chamber 101, for example, is always about the order of $10^{-7}$ Pa produced by evacuation using a very high vacuum pump, such as an ion pump. Further, for exchange of the sample 10, the sample 10 is preliminarily evacuated by a rough-suction pump in another space before the sample is inserted into the sample chamber 103. However, the degree of vacuum in the sample chamber 103 cannot be prevented from temporarily being lowered upon insertion of a sample into the sample chamber 103. In this situation, if the electron gun chamber 101 and the sample chamber 103 can be approximately independently evacuated, since the reduction of the degree of vacuum in the sample chamber 103 almost does not influence the electron gun chamber 101, sample exchange can be made even when the primary electron beam 201 is being emitted. Further, in a case where valves 41a, 41b, 41c and 41d are provided between the electron gun chamber 101 and the intermediate chamber 102 and the respective valves are closed, as the degree of vacuum in the electron gun does not change even upon sample exchange, the sample exchange can be made when the primary electron beam 201 is being emitted.

Note that in the present embodiment, a reflected electron and secondary electron detector having a hole for the electron beam passage may be used such that its detection surface is provided transverse to the electron beam axis 9, crossing the electron beam axis, in place of the detection means using the E×B deflector 8.

Note that in the present embodiment, the E×B deflector 8, the reflection plate 7 and the detector 13 are provided between the objective lens 4 and the electron source 1, however, the object of the present embodiment can also be attained by providing the E×B deflector 8, the reflection plate 7 and the detector 13 between the objective lens 4 and the sample 10.

Further, in the present embodiment, the sample 10 is set to a negative potential, however, even in a case where the sample 10 is grounded, if the relative potentials of the sample and another electrode are set in a similar manner to that of the present embodiment, the object of the present embodiment can be attained.

Further, in the present embodiment, the arrangement of the electron-optical systems is not especially limited. For example, the electron-optical systems may be arrayed in the form of a matrix, or may be arrayed in line.

Figure 4:
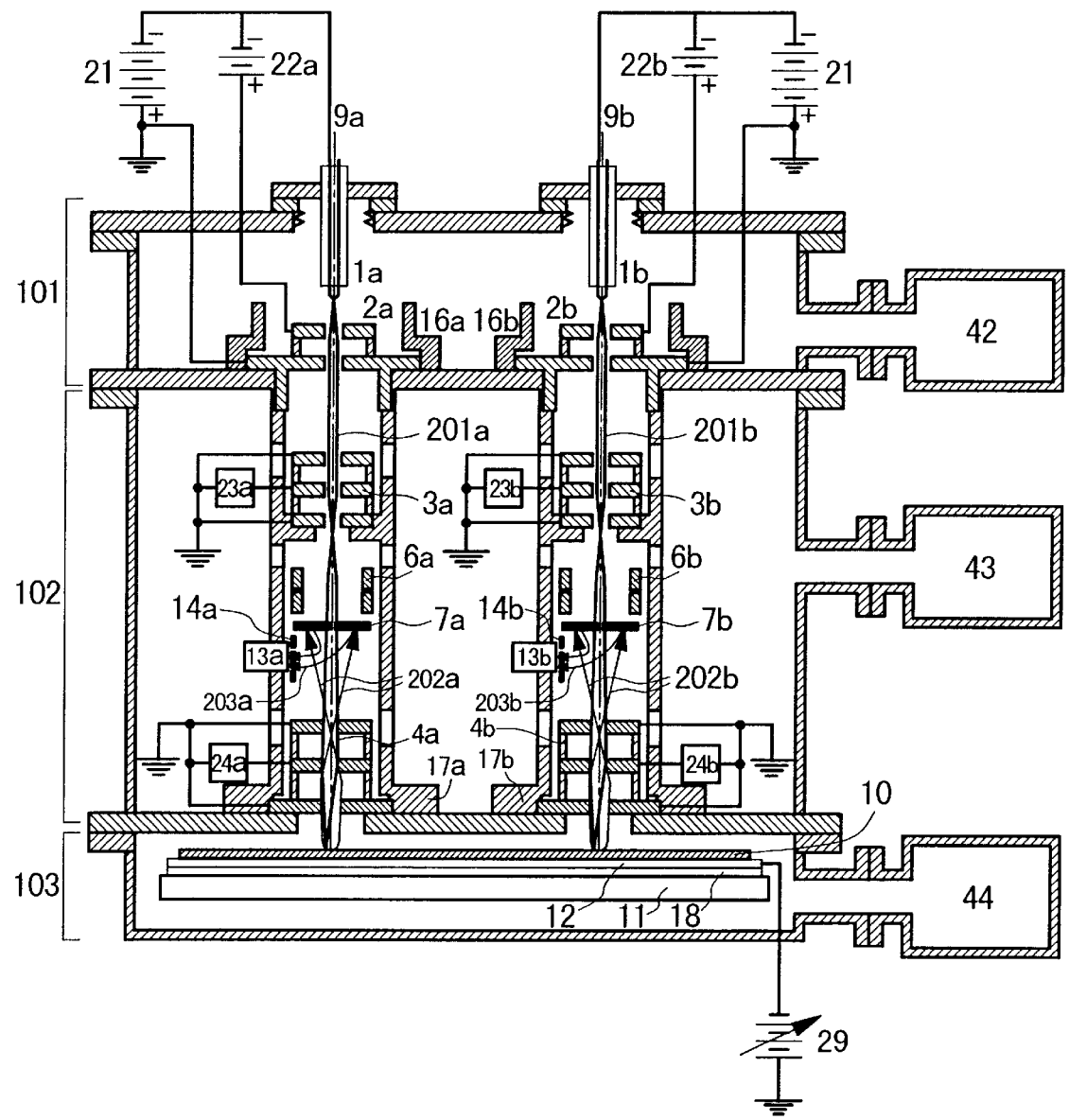
FIG. 4 is a cross-sectional diagram showing a second embodiment of the present invention.

In a second embodiment, an electrostatic lens is employed as an electronic lens. Since the size of the electrostatic lens can be smaller than that of a magnetic field lens, a large number of electron-optical systems can be arrayed in a limited space. FIG. 4 is a cross sectional view of the electron-optical systems of the present embodiment. Although only two electron-optical systems are shown in the figure, actually three or more electron-optical systems constitute the apparatus. The present embodiment corresponds to an electron-optical system to decelerate the primary electron beam 201 immediately before incidence on the sample. The detection system detects the second secondary electrons 202 caused by collision of the secondary electrons or reflected electrons 202 against the reflection plate 7. The secondary electrons or reflected electrons 202 emitted from the sample 10 are accelerated, then are focused by the objective lens 4, then while spreading in some range, they collide against the reflection plate 7, to generate the second secondary electrons 203. The second secondary electrons 203 are detected by the detector 13. The detector 13 is set to a positive potential and generates a detector electric field to attract the secondary electrons to the detector. The electrode has, as its structure here, a two-electrode electrostatic lens as the electron gun lens 2, and three-electrode lenses as the condenser lens 3 and the objective lens 4. In the present embodiment, the shielded electrodes 16 and 17 are also used as electronic lens supports. Since the positions of the electron gun lens 2, the condenser lens 3 and the objective lens 4 can be defined so as to be in contact with the inner periphery of the shielded electrode 16, the respective lenses can be positioned on the electron beam axis 9 with high accuracy. The field-emission type electron source 1 can be exchanged for another one by removing a flange having an insulator. The flange is capable of vacuum sealing in a high vacuum state, and has a diameter within a range from 34 mm to 70 mm.

Figure 5:
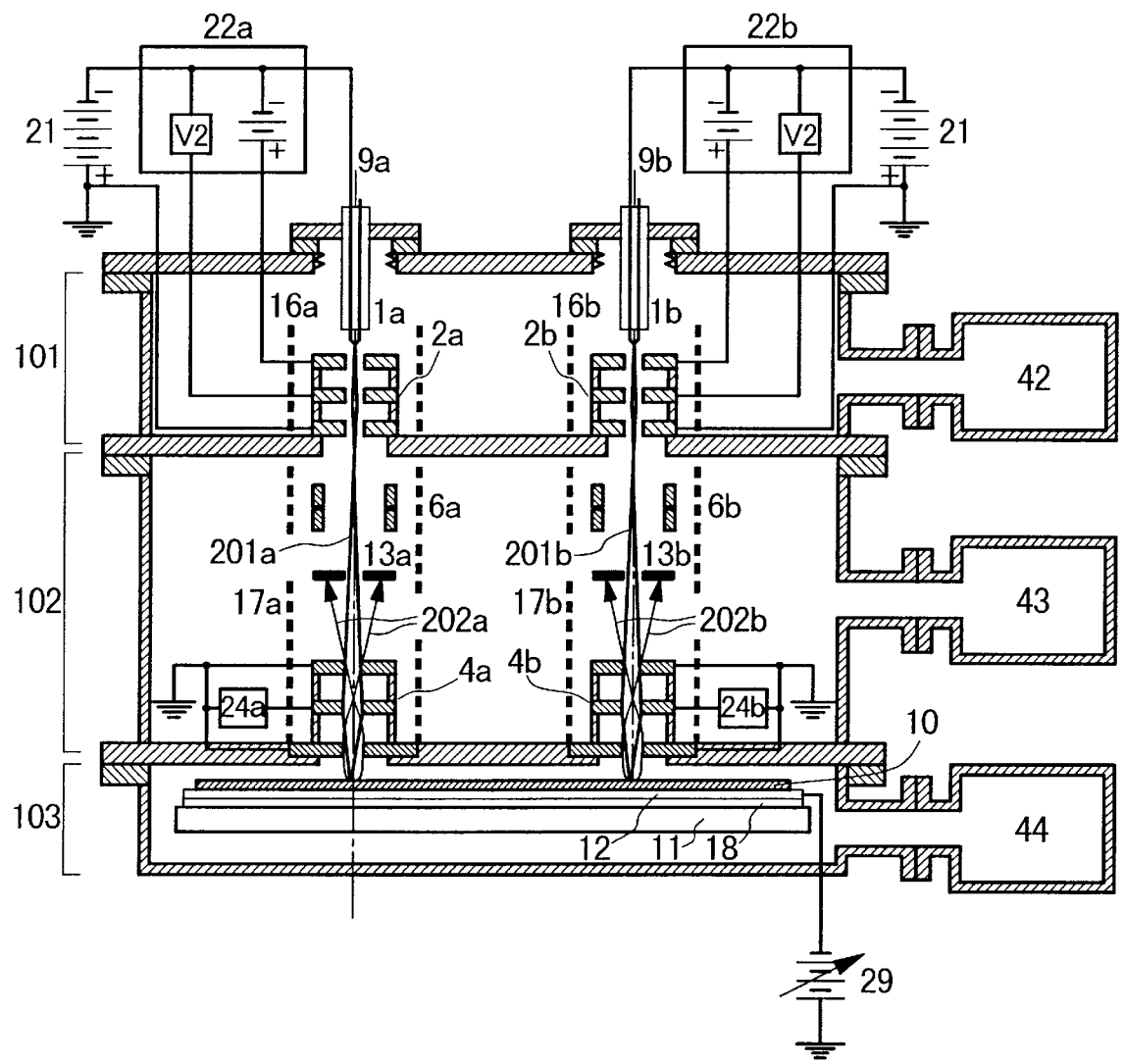
FIG. 5 is a cross-sectional diagram showing a third embodiment of the present invention.
Figure 6:
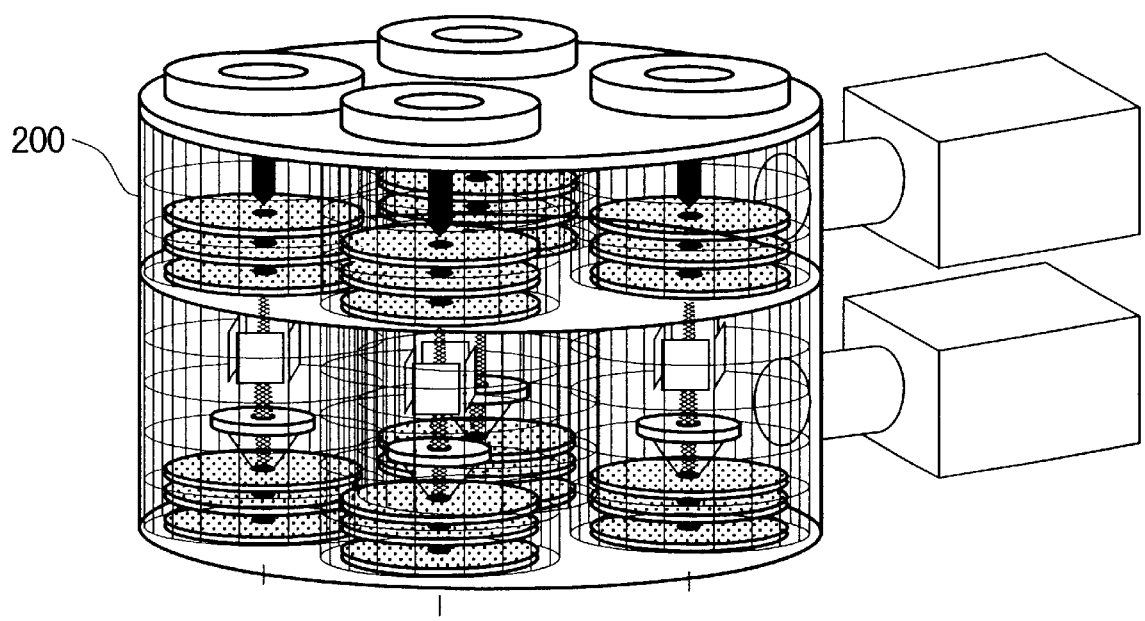
FIG. 6 is a perspective view as seen from an diagonally upper position showing the structure of the third embodiment of the present invention.

The electrode structure of the electrostatic lens may be any structure as long as the electrostatic lens can function as an electron gun lens with a pull-out electrode to cause the electron source 1 to emit electrons and an electrode to accelerate or decelerate the primary electron beam to an acceleration voltage, can function as a condenser lens to control the magnification of the electron-optic system, and can function as an objective lens to focus the primary electron beam on the sample. For example, it may be arranged that only one multistage lens with three or more electrodes has both the functions of a condenser lens and an objective lens or both the functions of an electron gun lens and a condenser lens. In a third embodiment, as shown in FIG. 5, one three-electrode electron gun lens 2 functions both as an electron gun lens and a condenser lens, thus the electron-optical system can be further downsized. FIG. 5 is a cross-sectional view of the structure of the electron-optical system of the present embodiment. FIG. 6 is a view from a diagonally upper position especially showing the electron gun chamber 101 and the intermediate chamber 102 of the present embodiment. Further, in the present embodiment, the detector 13 for the reflected electrons or secondary electrons 202 has a detection surface transverse to the electron beam axis 9, crossing the electron beam axis 9, and has a hole for the electron beam passage. The sample 10 is set to a negative voltage, and the reflected electrons or secondary electrons 202, emitted from the sample 10, are accelerated and detected. The detector 13 has a ring shape, or plural detectors are symmetrically provided with respect to the electron beam axis 9. In case of plural detectors, detection with discrimination of the emission direction from the sample can be made by selecting signals obtained from the detectors.

Figure 7:
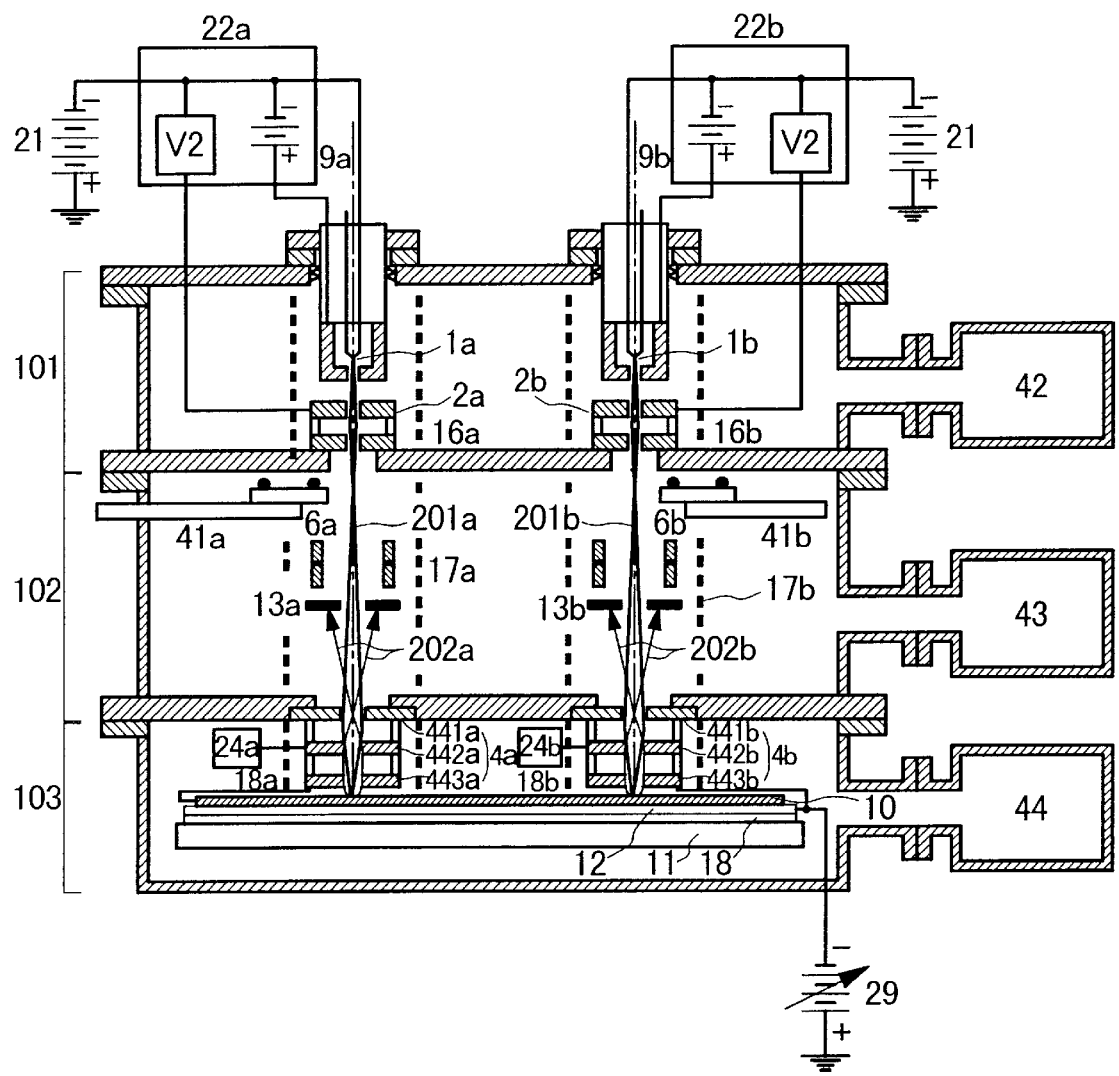
FIG. 7 is a cross-sectional diagram showing a fourth embodiment of the present invention.
Figure 17:
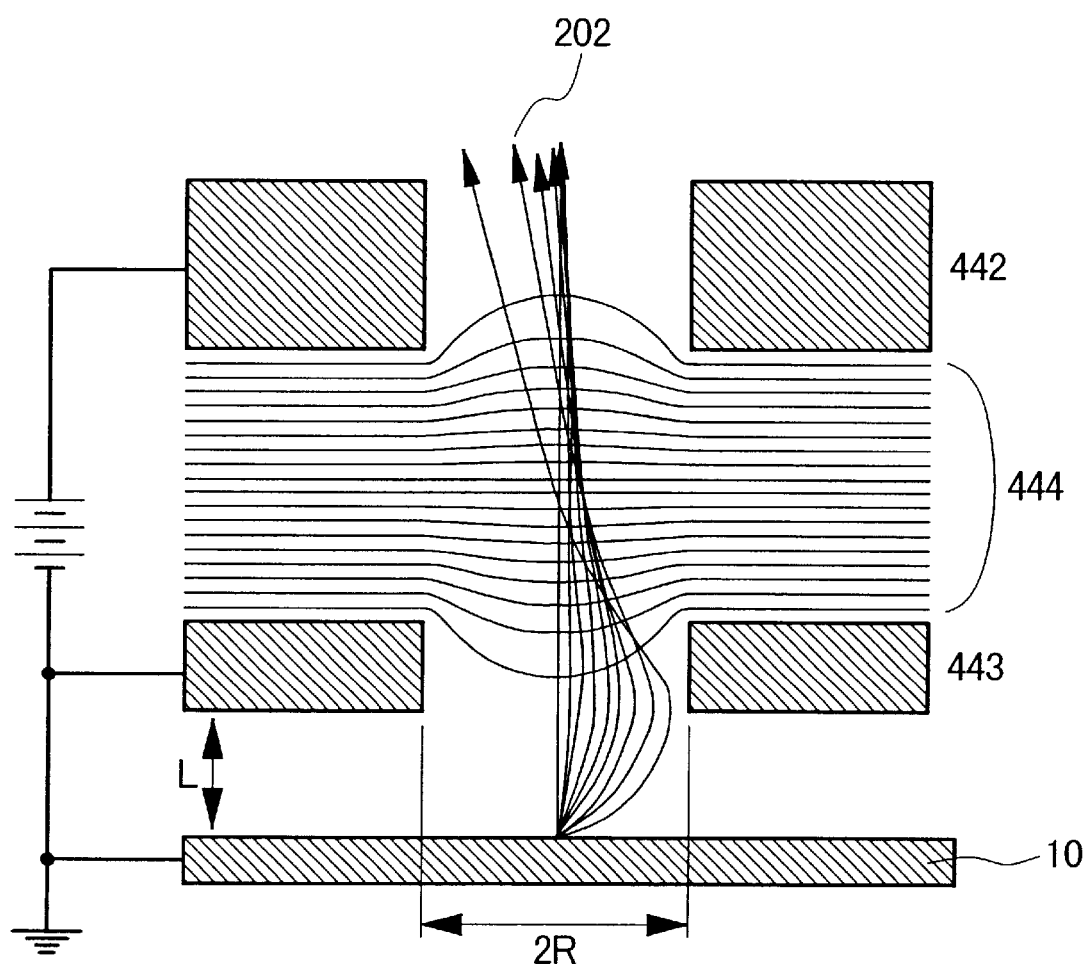
FIG. 17 is a diagram showing the trajectories of secondary electrons under a potential distribution in an electron-optical lens.

In a fourth embodiment shown in FIG. 7, an electrode 441 of the objective lens 4, closest to the electron source side, is set to a ground potential the same as that of the mirror body 200, and a counter electrode 443 for the sample is set to a negative potential the same as that of the sample. Further, by controlling the potential of an intermediate electrode 442, the primary electron beam is focused on the sample. In this structure, the secondary electrons and reflected electrons 202 are not acted upon by electric fields until they reach the counter electrode 443, then they pass through the counter electrode 443, and are accelerated toward the electron source in the direction of the electron beam axis 9. If the diameter of the opening of the counter electrode 443 is greater than the distance between the electrode and the sample, e.g., twice or greater, most of the electrons are accelerated without colliding against the counter electrode 443, and are detected by the detector 13. FIG. 17 shows the result of calculation of trajectories of secondary electrons under a potential distribution, obtained by a difference method, in a case where, as the distance between the counter electrode 443 and the sample 10, L=3 mm holds, at the diameter of the opening of the counter electrode, 2R=6 mm holds, and the counter electrode is set to the same potential to that of the sample 10, and +9.5 kv is applied to the intermediate electrode 442 with respect to the counter electrode 443. The potential distribution is as shown in an equipotential surface 444. The figure shows the trajectories of the secondary electrons 202 emitted to the sample at angles from 0° to 90° in steps of 10° with initial energy of 50 eV. If the opening is large, as the equipotential surface leaks to the sample side, the secondary electrons are accelerated upward before they reach the counter electrode. Accordingly, all the secondary electrons, including electrons emitted approximately parallel to the sample, can be directed to the electron source side without collision against the counter electrode.

Figure 8:
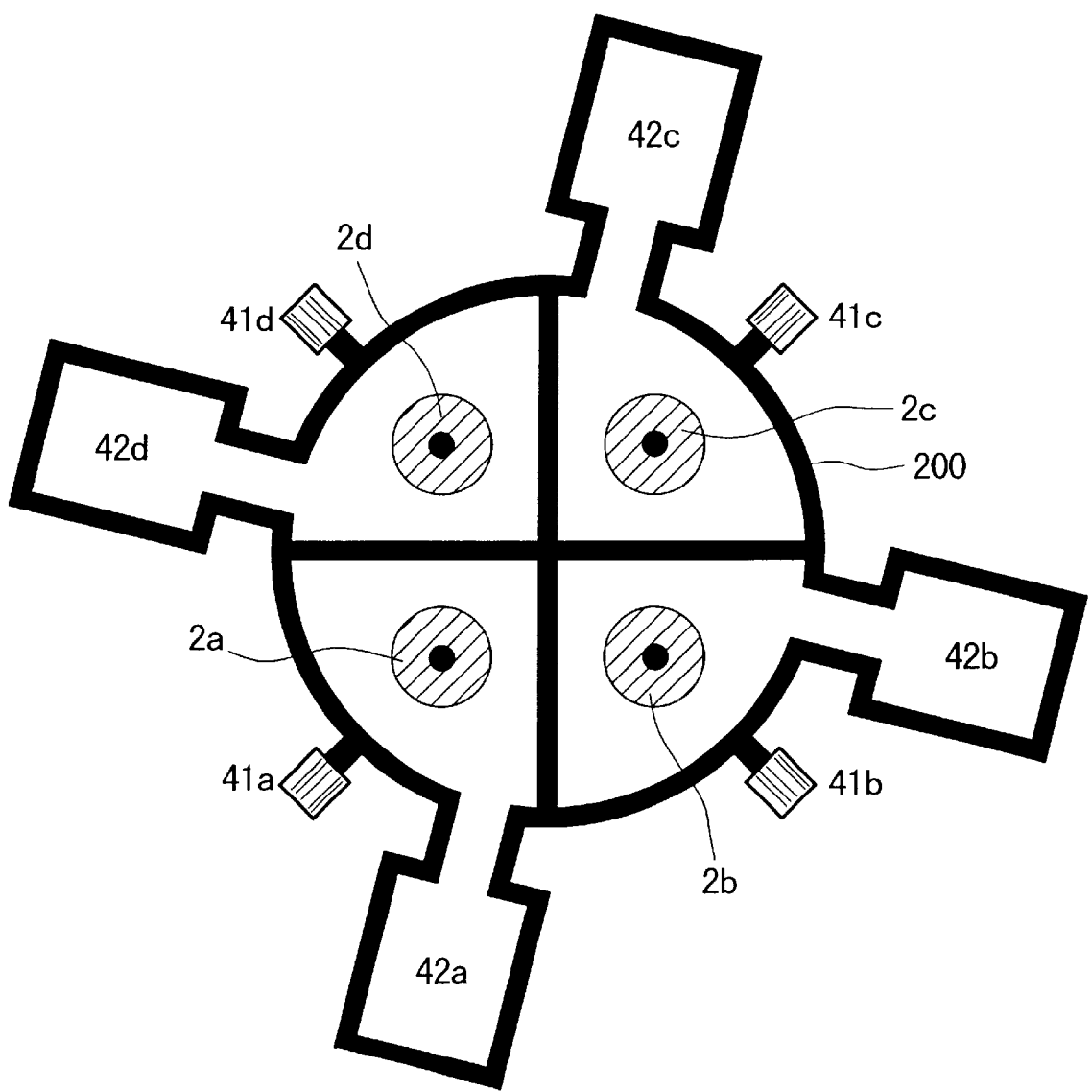
FIG. 8 is a diagram as seen from above showing the structure of the fourth embodiment of the present invention.

Further, FIG. 8 is a view from an upper position where the electron source 1 of the present embodiment is removed. The electron gun chamber 101 is partitioned for the respective electron sources, and the respective sections are respectively evacuated by independent vacuum pumps. The respective electron sources can be independently brought into an atmospheric pressure state by closing valves 41. This function enables exchange of the electron source 1 while maintaining the high vacuum states of the other electron sources.

Note that in the above-described first to fourth embodiments, three or four electron-optical systems are provided, however, even in a case where five or more electron-optical systems, e.g., ten sets of electron-optical systems, are provided, the object of the present invention can be easily attained.

Further, in the above-described second to fourth embodiments, the electrostatic lens actually has a shape to hide the insulator part from the electron beam passage, however, in the figures, the electrostatic lens has a flat plate shape for the sake of simplification.

Further, in the above-described second to fourth embodiments, the condenser lens power source 23 and the objective lens power source 24 are placed in a vacuum in the figures for convenience of explanation, however, actually, they are set out of the vacuum space.

Further, the construction to maintain the plural electron sources in high vacuum states and the construction to independently detect the secondary electrons and reflected electrons within the electron-optical systems of the present invention can be adapted to various electron-beam application devices such as an electron beam drawing device and a scan-type electron microscope using an electron beam. Further, the constructions are applicable to devices using charged particle beams including an ion beam as well as an electron beam. The construction to maintain plural charged particle sources in high vacuum states and the construction to detect charged particle beams secondarily generated by emission of a charged particle beam within respective charged particle beam optical systems can be realized by a similar construction of the present invention. In these cases, the present invention can be applied to a device having two or more electron-optical systems or charged particle optical systems.

As described above, the pattern inspection device according to the present invention is useful as an inspection device to inspect a circuit pattern on a semiconductor wafer, and, is appropriate to application to a pattern inspection device with the purpose of high-speed and accurate pattern inspection.

What is claimed:

1. A pattern inspection device having: at least three electron sources, electron lenses for focusing from said electron sources in different positions on a sample having patterns; deflectors that scan focused electron beams on said sample: detectors that detect secondary charged particles respectively generated from said sample as signals; a memory for storing at least three images of identical pattern portions of different chips obtained substantially simultaneously based on the detected signals; and a circuit that reads and compares the stored images and determines a defect.

2. A pattern inspection device having: three or more electron sources arranged in a same column; and means for scanning primary electron beams emitted from said three or more electron sources on a substrate where circuit patterns are formed by respectively using electron-optical systems, said device detecting secondary charged particles generated in the respective electron-optical systems within said electron-optical systems then obtaining images of circuit patterns, by accelerating the secondary charged particles generated from sample, comparing plural images and determining a defect in the circuit patterns substantially simultaneously.

3. A pattern inspection device having: three or more electron sources arranged in a same column; and means for scanning primary electron beams emitted from said three or more electron sources on a substrate where circuit patterns are formed by respectively using electron-optical systems, said device decelerating said primary electron beams immediately before they are emitted on said sample and accelerating secondary charged particles generated from said sample immediately after they are emitted from said sample, within the respective electron-optical systems, deflecting said secondary charged particles toward detectors by E×B deflectors provided between the sample and the detectors, and detecting the particles, thereby obtaining images of the circuit patterns, then comparing plural images and determining a defect in said circuit patterns.

4. A pattern inspection device having: three or more electron sources arranged in a same column; and means for scanning primary electron beams emitted from said three or more electron sources on a substrate where circuit patterns are formed by respectively using electron-optical systems, said device decelerating said primary electron beams immediately before they are emitted on said sample and accelerating secondary charged particles generated from said sample immediately after they are emitted from said sample, within the respective electron-optical systems, colliding said secondary charged particles against reflection plates to cause second secondary electrons, inducing said second secondary electrons to detectors set to a positive potential from said reflection plates and detecting the electrons, thereby obtaining images of the circuit patterns, comparing plural images and determining a defect in said circuit patterns.

5. The pattern inspection device according to claim 2, wherein the electron source is a field-emission type electron source.

6. The pattern inspection device according to claim 2, wherein the electron-optical system comprises only an electrostatic lens.

7. An electron-beam application device having at least three electron sources, emitting primary electron beams emitted from said electron sources on a sample by using respectively independent electron-optical systems arranged in a same column, wherein areas around said electron sources are evacuated by a vacuum pump different from that for an area around a sample chamber.

8. An electron-beam application device according to claim 7, wherein the areas around said electron sources and the area around the sample chamber are independently evacuated.

9. The electron-beam application device according to claim 7, wherein the areas around the electron sources and the area around the sample chamber are independently evacuated by providing valves corresponding to the number of electron sources between the electron sources and the sample chamber to block the passages through which the primary electron beams pass.

10. An electron-beam application device having at least three electron sources, said device emitting primary electron beams emitted from said electron sources on a sample by using respectively independent electron-optical systems arranged in a same column, wherein shielded electrodes are provided to confine electric fields or magnetic fields in the respective electron-optical systems within the same electron-optical systems, and wherein said shielded electrodes respectively have a structure to evacuate space inside each of the shielded electrode to a high degree of vacuum state.

11. An electron-beam application device having at least three electron sources, comprising: means for emitting primary electron beams emitted from said electron sources on a sample by using respectively independent electron-optical systems arranged in a same column; shield means for confining the primary electron beams within said respective electron-optical systems; and detection means for inducing secondary charged particles from the sample into said respective shield means and detecting the particles.

12. The electron-beam application device according to claim 11, wherein said shield means has a structure where shielded electrodes are provided to respectively surround a space from a position where secondary electrons generated from the sample to a position where the electrons are detected by a detector, and wherein said shielded electrodes have a shape enabling evacuation of a space inside said shielded electrode to a high degree of vacuum.

13. An electron-beam application device having; three or more electron sources; emitting apparatus which emits primary electron beams emitted from said three or more electron sources on a sample by using respectively independent electron-optical systems; detecting apparatus which detects secondary electrons or reflected electrons generated from said sample by using detectors independently provided in the respective electron-optical systems, wherein the secondary electrons or reflected electrons generated from said sample are collected by the detectors within the same electron-optical systems by accelerating apparatus which accelerates the secondary electrons or reflected electrons toward the electron source side in a direction of electron beam axes immediately after they are emitted from said sample and detecting the electrons.

14. An electron-beam application device having: three or more electron sources, emitting apparatus which emits primary electron beams emitted from said three or more electron sources on a sample by using respectively independent electron-optical systems; and detecting apparatus which detects secondary electrons or reflected electrons generated from said sample by detectors independently provided in the respective electron-optical systems, wherein the secondary electrons or reflected electrons are collected by the detectors in the same electron-optical systems by accelerating apparatus which accelerates the secondary electrons or reflected electrons generated from said sample toward the electron source side in a direction of electron beam axes immediately after the electrons are emitted from the sample and colliding the electrons against reflection plates thereby causing second secondary electrons and by inducing apparatus which induces said second secondary electrons to the detectors set to a positive potential higher than that of said reflection plates and detecting the electrons.

15. The electron-beam application device according to any one of claims 7, 9 to 11 and 13 and 14, wherein the electron source is a field-emission type electron source.

16. The electron-beam application device according to any one of claims 7, 10, 11, 13 and 14, wherein the electron-optic system comprises only an electrostatic lens.

* * * * *